US012213781B2

(12) United States Patent
Stankovic et al.

(10) Patent No.: US 12,213,781 B2
(45) Date of Patent: Feb. 4, 2025

(54) SYSTEMS AND METHODS FOR MICRO-OPTICAL COHERENCE TOMOGRAPHY IMAGING OF THE COCHLEA (71) Applicant: The General Hospital Corporation, Boston, MA (US)

(72) Inventors: Konstantina Stankovic, Boston, MA (US); Guillermo J. Tearney, Cambridge, MA (US); Janani Iyer, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 314 days.

(21) Appl. No.: 16/049,362

(22) Filed: Jul. 30, 2018

(65) Prior Publication Data
US 2019/0029570 A1 Jan. 31, 2019

Related U.S. Application Data (60) Provisional application No. 62/538,491, filed on Jul. 28, 2017.

(51) Int. Cl.
*A61B 5/12* (2006.01)
*A61B 5/00* (2006.01)
(Continued)

(52) U.S. Cl.
CPC .............. *A61B 5/12* (2013.01); *A61B 5/0066* (2013.01); *A61B 5/0084* (2013.01);
(Continued)

(58) Field of Classification Search
CPC ......... A61B 5/12; A61B 5/0066; A61B 5/084; A61B 5/4884; A61B 2090/3614; A61B 2562/0233
See application file for complete search history.

(56) References Cited

U.S. PATENT DOCUMENTS 9,020,613 B2 4/2015 Taylor et al.
9,345,397 B2 5/2016 Taylor et al.
(Continued)

FOREIGN PATENT DOCUMENTS

JP 2015198723 * 11/2015
WO WO-2017049085 A1 * 3/2017 ........... A61B 5/0066

OTHER PUBLICATIONS

Gonzalez-Calle, Evaluation of Effects of Electrical Stimulation in the Retina with Optical Coherence Tomography,2016 (Year: 2016).*
(Continued)

*Primary Examiner* — Joseph M Santos Rodriguez
*Assistant Examiner* — Brooke Lyn Klein
(74) *Attorney, Agent, or Firm* — Quarles & Brady LLP (57) ABSTRACT An optical coherence tomography (OCT) imaging tool including an optical waveguide having a proximal end and a distal end, at least a portion of the optical waveguide disposed at the distal end of the optical waveguide having an increased elasticity than a proximal portion of the optical waveguide; a sheath surrounding at least a portion of the optical waveguide; and an optical probe coupled to the optical waveguide, the optical probe including: an optical element coaxially aligned with a central axis of the distal end of the optical waveguide, the optical element being configured to rotate about the central axis and redirect light emitted by the optical waveguide toward a circumference of the optical probe from the central axis, and the focusing element being disposed within a housing.

18 Claims, 9 Drawing Sheets

(51) Int. Cl.
    *A61N 1/05*     (2006.01)
    *A61N 1/36*     (2006.01)
    *A61B 90/00*     (2016.01)

(52) U.S. Cl.
    CPC .......... *A61B 5/4884* (2013.01); *A61N 1/0541* (2013.01); *A61N 1/36038* (2017.08); *A61B 2090/3614* (2016.02); *A61B 2090/3735* (2016.02); *A61B 2562/0233* (2013.01)

(56) References Cited

U.S. PATENT DOCUMENTS

| | | | |
|---|---|---|---|
| 9,597,503 B2* | 3/2017 | Risi | A61N 1/0541 |
| 10,314,491 B2 | 6/2019 | Cui et al. | |
| 10,584,954 B2 | 3/2020 | Tearney et al. | |
| 2001/0055462 A1* | 12/2001 | Seibel | A61B 1/00048 385/33 |
| 2006/0114473 A1* | 6/2006 | Tearney | G02B 23/2453 356/479 |
| 2007/0100336 A1* | 5/2007 | McFarlin | A61B 17/1626 606/45 |
| 2008/0260342 A1* | 10/2008 | Kuroiwa | A61B 5/0066 385/133 |
| 2011/0098572 A1* | 4/2011 | Chen | A61B 5/0066 600/463 |
| 2011/0218403 A1* | 9/2011 | Tearney | A61B 5/0084 600/165 |
| 2012/0071890 A1 | 3/2012 | Taylor et al. | |
| 2012/0172893 A1* | 7/2012 | Taylor | A61F 11/004 606/130 |
| 2012/0287420 A1* | 11/2012 | McLaughlin | A61N 5/0622 356/72 |
| 2013/0060131 A1 | 3/2013 | Oghalai et al. | |
| 2013/0331689 A1* | 12/2013 | Le | A61B 5/0084 600/425 |
| 2014/0039261 A1 | 2/2014 | Kang et al. | |
| 2018/0042466 A1 | 2/2018 | Kang et al. | |
| 2018/0303327 A1* | 10/2018 | Yamada | A61B 1/07 |
| 2018/0333205 A1* | 11/2018 | Paamand | G01K 11/3206 |
| 2019/0200868 A1 | 7/2019 | Psaltis et al. | |
| 2019/0353841 A1* | 11/2019 | Sillard | G02B 6/0288 |

OTHER PUBLICATIONS

Electrical Comms Data (ECD), "Singlemode vs multimode optical fibre", 2014 (Year: 2014).*
Boppart et al., In Vivo Cellular Optical Coherence Tomography Imaging, Nature Medicine, 1998, 4(7):861-865.
Cheon et al., 3D Optical Coherence Tomography Image Registration for Guiding Cochlear Implant Insertion, Proceedings of SPIE, 2014, vol. 8926, p. 89261Z, 6 pages.
Fujimoto et al., Optical Coherence Tomography: An Emerging Technology for Biomedical Imaging and Optical Biopsy, Neoplasia, 2000, 2(1-2):9-25.
Gurbani et al., Robot-Assisted Three-Dimensional Registration for Cochlear Implant Surgery Using a Common-Path Swept-Source Optical Coherence Tomography Probe, Journal of Biomedical Optics, 2014, 19(5):057004, 8 pages.
Huang et al., Optical Coherence Tomography, Science, 1991, 254(5035):1178-1181.
Iyer et al., Micro-Optical Coherence Tomography of the Mammalian Cochlea, Scientific Reports, Sep. 16, 2016, 6:33288, 10 pages.
Leitgeb et al., Extended Focus Depth for Fourier Domain Optical Coherence Microscopy, Optics Letters, 2006, 31(16):2450-2452.
Liu et al., Method for Quantitative Study of Airway Functional Microanatomy Using Micro-Optical Coherence Tomography, PloS One, 2013, 8(1):e54473, 8 pages.
Povazay et al., Submicrometer Axial Resolution Optical Coherence Tomography, Optics Letters, 2002, 27(20):1800-1802.
Spaide et al., Enhanced Depth Imaging Spectral-Domain Optical Coherence Tomography, American Journal of Ophthalmology, 2008, 146(4):496-500.
Yin et al., µOCT Imaging Using Depth of Focus Extension by Self-Imaging Wavefront Division in a Common-Path Fiber Optic Probe, Optics Express, 2016, 24(5):5555-5564.

* cited by examiner

Radius of Curvature of Scala Tympani at Various Points

| Angle from round window | Radius of curvature | Diameter of scala tympani |
|---|---|---|
| 0° | 6mm | 4mm x 2mm |
| 90° | 4mm | 4mm x 2mm |
| 180° | 3.75mm | 4mm x 2mm |
| 270° | 3mm | 3mm x 2mm |
| 360° | 2mm | 3mm x 2mm |

SYSTEMS AND METHODS FOR MICRO-OPTICAL COHERENCE TOMOGRAPHY IMAGING OF THE COCHLEA

CROSS-REFERENCE TO RELATED APPLICATIONS

This application is based on, and claims the benefit of U.S. Provisional Patent Application No. 62/538,491, filed Jul. 28, 2017, which is hereby incorporated herein by reference in its entirety for all purposes.

STATEMENT REGARDING FEDERALLY SPONSORED RESEARCH

N/A

BACKGROUND

The field of auditory research has been hindered by the fact that no techniques exist for visualizing the cells and auditory nerve fibers that facilitate hearing from within the cochlea in living humans. For example, the only sources of knowledge on the effects of the inner ear's deterioration on hearing include research using cadaveric human temporal bone specimens and animal models of sensorineural hearing loss. Currently, inner ear biopsy is impossible without damaging the delicate inner ear structures that facilitate hearing.

One factor that has contributed to this lack of techniques for visualizing these structures within the cochlea is the cochlea's anatomical structure. For example, the cochlea is extremely well protected, as it is deeply encased in the densest bone in the in the human body (i.e., the otic capsule), deep within the temporal bone. As another example, the human cochlea has a relatively complex snail shell shape that coils about two and a half times with a relatively tight (and diminishing) radius of curvature.

Additionally, the dimensions of the cochlea are relatively small (i.e., on the order of a few millimeters in size), with anatomical structures that exist on the single micron scale. For example, the only point of entry that is accessible without disturbing the middle ear ossicular chain and/or disturbing the cochlea's bony capsule is the cochlea's round window, which is roughly in the range of 1.5 to 1.8 millimeters (mm) in diameter in humans. As another example, the scala tympani, one of the cochlea's three fluid-filled lumina and the lumen that the round window opens into, generally ranges in diameter from about 3-5 mm×1.5-2.5 mm at the round window to roughly 0.6 mm at the cochlea's apex. As yet another example, the cochlea's radius of curvature ranges from 6 mm at its base to roughly 1 mm at its apex. As still another example, structures of relevance to sensorineural hearing loss, such as inner and outer hair cells, auditory nerve fibers, spiral ganglion neuron cell bodies, and Reissner's membrane, are located within a 1.8 mm-diameter radius of the scala tympani's center in the cochlea's base, and the structures themselves are microns in size.

These anatomical limitations have significantly hindered the development of technology suited for investigating the interior and microstructures of the cochlea. For example, while conventional non-invasive imaging modalities (e.g., MRI and CT) can image the cochlea's interior, the resolution is insufficient for providing diagnostic information as these modalities generally cannot resolve anatomical features with sizes on the order of a microns.

Accordingly, systems and methods for imaging of the cochlea are desirable.

SUMMARY

In accordance with some embodiments of the disclosed subject matter, systems and methods for micro-optical coherence tomography imaging of the cochlea are provided.

In accordance with some embodiments of the disclosed subject matter, an optical coherence tomography imaging tool is provided, comprising: an optical waveguide having a proximal end and a distal end, at least a portion of the optical waveguide disposed at the distal end of the optical waveguide having an increased elasticity than the proximal end of the optical waveguide; a sheath surrounding at least a portion of the optical waveguide; and an optical probe coupled to the optical waveguide, the optical probe comprising: an optical element coaxially aligned with a central axis of the distal end of the optical waveguide, the optical element being configured to rotate about the central axis and redirect light emitted by the optical waveguide toward a circumference of the optical probe from the central axis, and the focusing element being disposed within a housing.

In some embodiments, the optical waveguide comprises an optical fiber core and a refractive index trench coaxially surrounding the optical fiber core.

In some embodiments, the proximal end of the optical waveguide has a first diameter, the optical waveguide tapering to a second diameter that is smaller than the first diameter such that the portion of the optical waveguide is the second diameter.

In some embodiments, the portion of the optical waveguide having an increased elasticity comprises an optical fiber surrounded by a cladding which is etched to remove material around the circumference of the optical waveguide, thereby decreasing the Young's modulus of elasticity of the portion of the optical waveguide.

In some embodiments, the optical probe further comprises a second optical waveguide disposed between the distal end of the optical waveguide and the optical element, wherein the second optical waveguide is configured to act as a mirror tunnel that causes light emitted from the distal end of the optical waveguide and received at a proximal end of the second optical waveguide with a single propagation mode to be emitted from a distal end of the second optical waveguide with multiple propagation modes toward the optical element.

In some embodiments, the optical waveguide comprises a single mode optical fiber, and the second optical waveguide comprises a multimode optical fiber.

In some embodiments, the optical element is a prism, and the optical probe further comprises a spacer disposed at the distal end of the second optical waveguide, and a gradient index lens disposed between the spacer and the optical element.

In some embodiments, the optical element is a polished ball lens, and the optical probe further comprises a spacer disposed between the second optical waveguide and the polished ball lens.

In some embodiments, the optical element has a cylindrical bore coaxially aligned with the optical waveguide, and an angled reflective surface that redirects the light emitted by the optical waveguide toward the circumference of the optical probe from the central axis as a beam with a generally annular-shaped profile.

In some embodiments, the imaging tool further comprises: a stimulator configured to provide stimulation to a portion of an auditory nerve of a subject; and a conductor coupled to the stimulator, wherein the conductor is configured to transmit a signal from a controller to the stimulator.

In some embodiments, the stimulator comprises an electrode disposed at an exterior surface of the housing.

In some embodiments, the stimulator comprises an optrode disposed at an exterior surface of the housing.

In some embodiments, the conductor is integrated into the sheath.

In some embodiments, the optical waveguide is disposed within a first lumen of the sheath, and the conductor is disposed within a second lumen of the sheath.

In some embodiments, the optical waveguide is configured to rotate within the sheath.

In some embodiments, the imaging tool further comprises a driveshaft coupled to the optical element and surrounding the optical waveguide such that rotation of the driveshaft causes the optical waveguide to rotate within the sheath and causes the optical element to rotate within the housing.

In some embodiments, the imaging tool further comprises a micromotor coupled to the optical element, wherein the micromotor is configured to rotate the optical element within the housing.

In accordance with some embodiments of the disclosed subject matter, a method for micro-optical coherence tomography imaging of a human cochlea in vivo is provided, the method comprising: emitting light into a proximal end of an optical waveguide toward a distal end of the optical waveguide that is coupled to an optical probe inserted into the cochlea through the round window of the cochlea, the optical imaging probe comprising: an optical element coaxially aligned with a central axis of a distal end of the optical waveguide, the optical element being configured to rotate about the central axis and redirect light emitted by the optical waveguide toward a circumference of the optical probe from the central axis, and the focusing element being disposed within a housing; causing the optical imaging probe to emit light received from the distal end of the optical waveguide toward an interior of the cochlea; causing the optical imaging probe to receive reflected light from the cochlea and transmit the reflected light toward a proximal end of the optical waveguide; receiving, using an optical coherence tomography system, the reflected light from the optical imaging probe; generating a two dimensional image of a portion of the cochlea surrounding the optical probe based on the reflected light received from the optical imaging probe; and causing the two dimensional image of the portion of the cochlea surrounding the optical probe to be presented, the two dimensional image being indicative of a distance between an outer surface of the optical probe and a wall of the cochlea.

In some embodiments, the method further comprises causing a series of two dimensional images to be generated based on reflected light received from the optical probe during a pullback operation in which the optical probe is extracted from the cochlea.

In some embodiments, the method further comprises generating a three-dimensional reconstruction of the scala tympani of the cochlea based on the series of two dimensional images.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with some embodiments of the disclosed subject matter, mechanisms (which can include, for example, systems and methods) for micro-optical coherence tomography imaging of the cochlea are provided.

In some embodiments, the mechanisms described herein can facilitate cellular-level visualization of the interior of the cochlea in humans, which can allow otologists to directly associate intracochlear pathology with hearing ability in patients with sensorineural hearing loss. This can facilitate more precise and accurate diagnosis based on disease etiology and progression, in addition to providing personalized treatment recommendations.

In some embodiments, the mechanisms described herein can be used to identify patients who are specifically eligible for treatment for sensorineural hearing loss via gene therapy and other biologic therapies, such as small molecule therapeutics. For example, image data generated using the mechanisms described herein can be used to evaluate the structures of the cochlea. As another example, functional information (e.g., gathered based on stimulation delivered to one or more structures of the cochlea, and/or gathered from sensors placed near one or more structures of the cochlea) generated using the mechanisms described herein can be used to determine evaluate the behavior of the structures of the cochlea.

In some embodiments, the mechanisms described herein can be used to perform image-guided insertion of electrode arrays during surgical installation of cochlear implants, which, despite their reputation as the most successful neural prosthesis to date, are positioned blindly due to lack of a minimally invasive imaging tool that provides real-time visual feedback.

In some embodiments, despite the fact that the cochlea is well protected within the temporal bone, the mechanisms described herein can include insertion of an optical probe directly into the cochlea, via, for example, the round window. While penetration into the cochlea via the round window is often used during placement of electrode arrays in patients receiving cochlear implants, the mechanisms described herein can be used to generate images of the cochlea's features via insertion of a small diameter optical probe through the round window.

In some embodiments, although the cochlea has a relatively complex shape with a small (and diminishing) radius of curvature, the mechanisms described herein can nevertheless be used to implement a relatively flexible, and bend-insensitive (e.g., such that a portion of the mechanisms can bend with relatively low bending losses) optical probe that can safely be inserted relatively deep into the cochlea. Additionally, in some embodiments, the mechanisms described herein can be used to implement an optical probe with a relatively short rigid portion that houses inflexible optical elements. In such embodiments, a rigid portion that is relatively short can facilitate relatively deep insertion into the cochlea by reducing the likelihood that the rigid portion is too long to navigate the spiral shape of the cochlea.

In some embodiments, as structures of the cochlea are relatively small in cross-sectional size (e.g., having lumina on the order of a few millimeters) and the most convenient access is only a few millimeters across (e.g., the round window is generally about 1.5 mm in diameter in humans and no larger than 2 mm), the mechanisms described herein can be used to implement an optical probe with a relatively small diameter (e.g., on the order of microns to a few millimeters). Additionally, in some embodiments, as the cochlea includes features on the scale of microns, the mechanisms described herein can be used to implement a diagnostic tool that can resolve micron-scale features, while still achieving a depth of focus on the order of millimeters.

Figure 1:
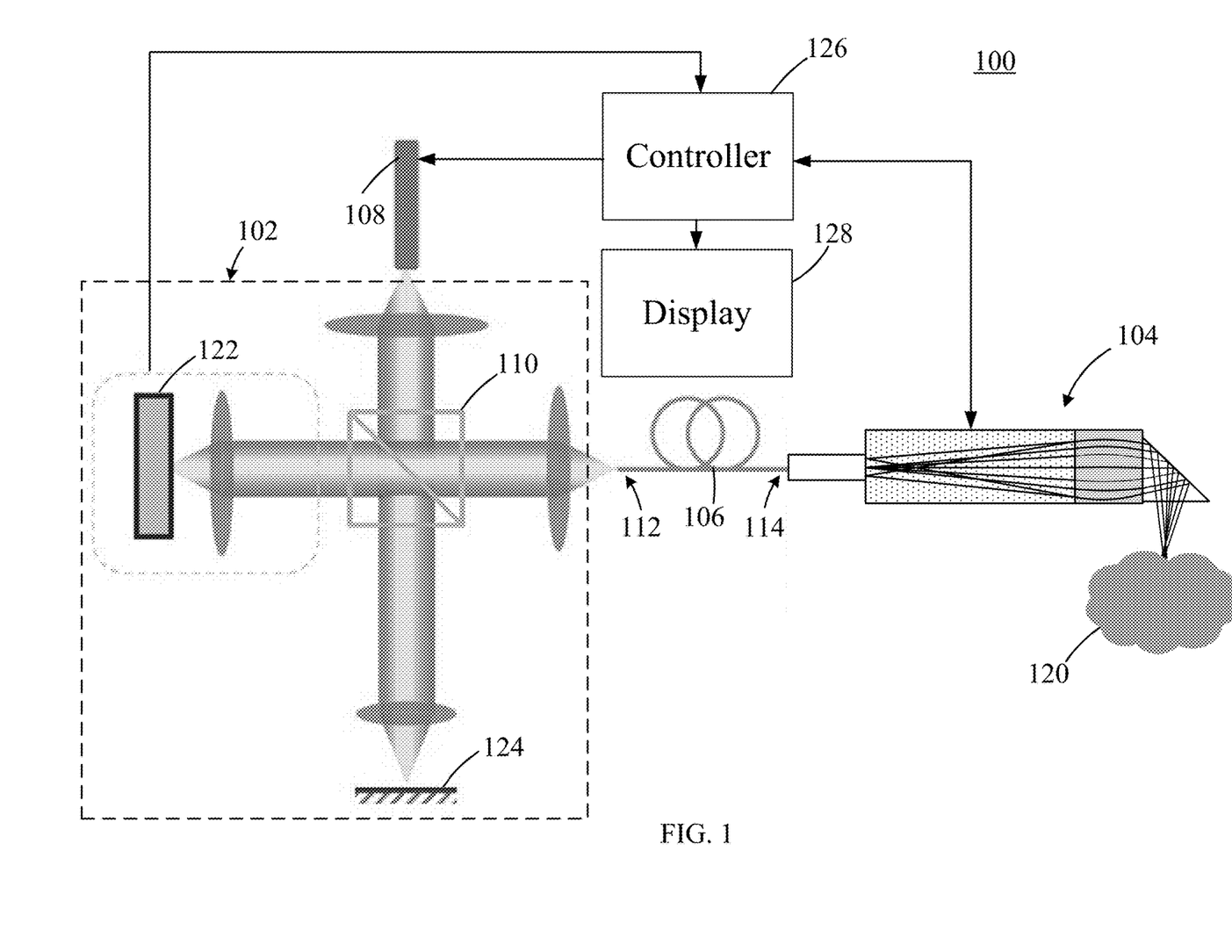
FIG. 1 shows an example of a system for micro-optical coherence tomography imaging of the cochlea in accordance with some embodiments of the disclosed subject matter.

FIG. 1 shows an example 100 of a system for micro-optical coherence tomography (μOCT) imaging of the cochlea in accordance with some embodiments of the disclosed subject matter. As shown in FIG. 1, optical system 100 includes an external optical assembly 102 optically coupled to an optical imaging probe 104 via an optical waveguide 106 (e.g., an optical fiber, an optical fiber bundle, separate optical fibers, etc.). Optical imaging probe 104 can take various forms, for example as described below in connection with FIGS. 4A to 4D, which can be disposed (e.g. rotatably disposed) within a housing for imaging structures such as a luminal sample (e.g. in the cochlea, in other small diameter lumens) in a subject such as a human. In optical system 100, external optical assembly 102 can be configured to receive source light from a light source 108, and can include a beam splitter 110 to reflect a portion of the light from light source 108 into a proximal end 112 of the optical waveguide 106, and another portion of the light from light source 108 onto a reference reflector 124. In the system of FIG. 1, light source 108 can be a broadband light source, such as a broadband laser, or a laser configured to sweep wavelengths in the visible and/or near-infrared spectrum.

In some embodiments, optical waveguide 106 of optical system 100 can be configured to transmit the source light from proximal end 112 to a distal end 114 of optical waveguide 106, which is coupled to optical imaging probe 104 and arranged to project the source light from distal end 114 onto an optical component within optical imaging probe 104. Optical component can be implemented with a reflective surface configured to reflect the source light emitted from distal end 114 of optical waveguide 106 onto a sample 120 (e.g., a portion of the scala tympani within the cochlea of a human subject).

In some embodiments, distal end 114 of optical waveguide 106 can be arranged to receive reflected light from sample 120 via the reflective surface. The reflected light can then be transmitted along optical waveguide 106 from distal end 114 to proximal end 112. Light reflected from sample 120 that is transmitted to proximal end 112 of optical waveguide 106 can then be transmitted through beam splitter 110 to an optical detector 122, such as a CCD image sensor, a CMOS image sensor, photodiodes (e.g., made of silicon, germanium, InGaAs, lead sulfide, or other materials), photocells, photoresistors, phototransistors, etc. As described above, a portion of the source light output by light source 108 can be transmitted through beam splitter 110 to reference reflector 124, which reflects the incident light and directs it back to beam splitter 110, which reflects the reference light to optical detector 122 such that optical detector 122 receives both reference source light reflected from reference reflector 124 and light reflected from sample 120. Interference (e.g., constructive and/or destructive interference) between the reference light and the light reflected from sample 120 allows discrimination between signals from different depths, using any suitable optical coherence tomography techniques, such as optical frequency domain (OFDI) techniques, spectral domain OCT techniques, Fourier domain OCT techniques, etc., as constructive interference between the reference signal and sample signal indicates that the signals have traveled equivalent distances, and the depth of a particular received signal can be calculated based on the interference of the signals.

In some embodiments, a controller 126 can coordinate operation of one or more of optical imaging probe 104, light source 108, optical detector 122, and a display 128. Controller 126 can be in wired (e.g., via Ethernet, USB, CAN, etc.) and/or wireless (e.g., via Bluetooth®, WiFi, etc.) communication with optical imaging probe 104, light source 108, optical detector 122, and/or display 128.

In some embodiments, controller 126 can receive a signal from optical detector 122 based on the light reflected off reflective surface 118 from sample 120, and can generate two dimensional and/or three-dimensional images representing morphological data (e.g., as shown in, and described below in connection with, FIGS. 8A and 8B). For example, optical system 100 can use an optical frequency domain imaging technique or combination of techniques to generate cross-sectional morphological data, and can generate a three-dimensional representation (e.g., of a portion of a luminal organ or passageway of a patient) by combining information from sequential cross-sections. As another example, optical system 100 can use a spectral domain imaging technique or combination of techniques to generate such cross-sectional and/or three-dimensional representations. Additionally or alternatively, in some embodiments, controller 126 can output data corresponding to the cross-sectional morphological data and another computing device can use the cross-sectional morphological data to generate the three-dimensional representation.

Note that, although not shown in FIG. 1, one or more portions of optical imaging probe 104 can be rotated using any suitable technique or combination of techniques to generate image data around a circumference of optical imaging probe 104. For example, optical imaging probe 104 can be rotated by a driveshaft surrounding optical waveguide 106 that is used to rotate both optical waveguide 106 and optical imaging probe 104. In such an example, the driveshaft can be rotated by an optical rotary joint or other suitable device, which may be provided between distal end 114 of optical waveguide 106 and optical imaging probe 104. As another example, a motor can be associated with optical imaging probe 104, and the motor can rotate a portion of the optics within probe 104 in order to provide rotational scanning.

Figure 2:
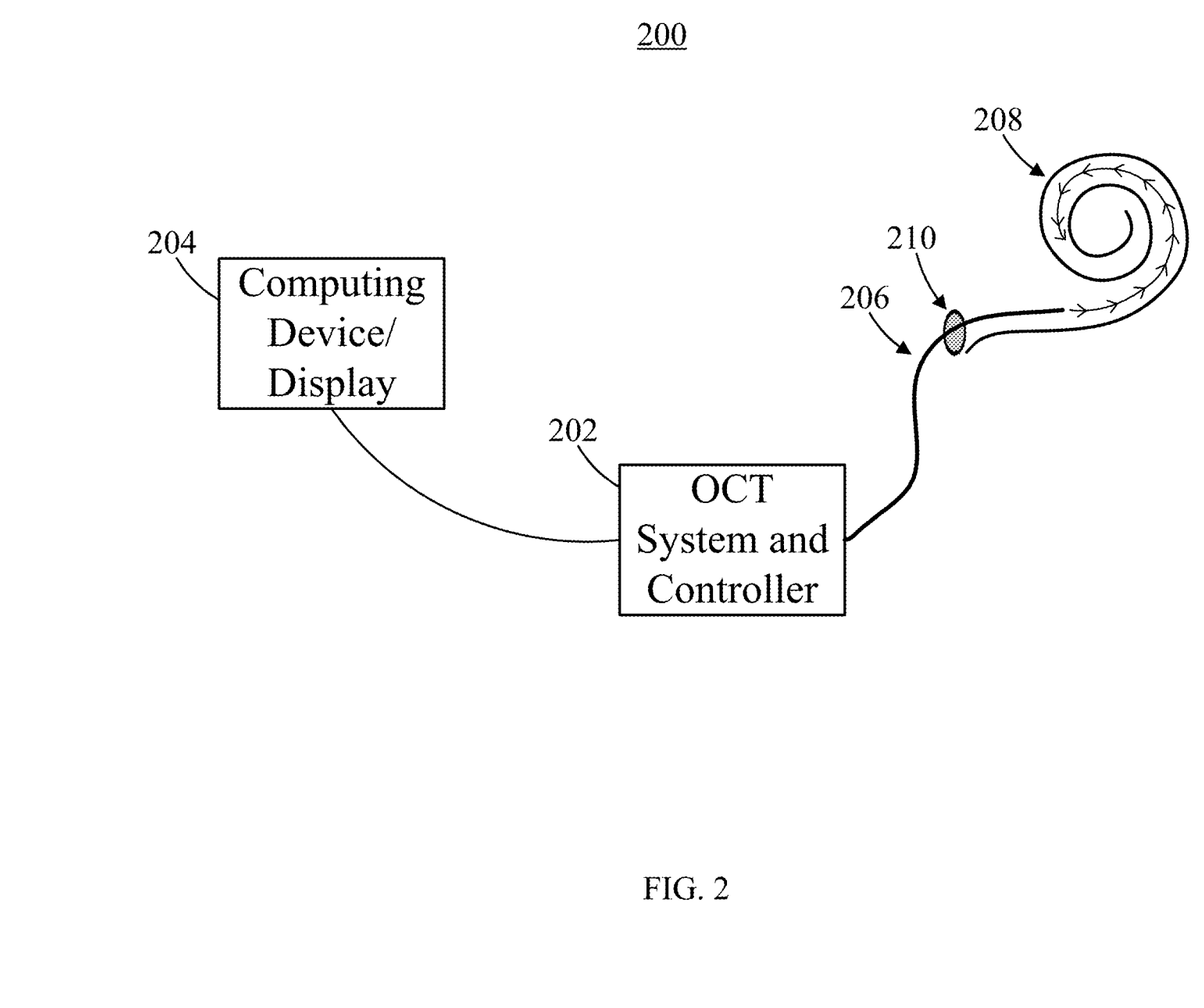
FIG. 2 shows an example of a micro-optical coherence tomography system being used to image the cochlea system of a subject via the round window in accordance with some embodiments of the disclosed subject matter.

FIG. 2 shows an example 200 of a micro-optical coherence tomography system being used to image cochlear structures of a subject via the round window in accordance with some embodiments of the disclosed subject matter. As shown in FIG. 2, an OCT system 202 and controller (e.g., as described above in connection with system 100 of FIG. 1) can be coupled to a computing device and/or external display 204 (e.g., in addition to, or in lieu of, display 128 described above in connection with FIG. 1) such that data generated using an imaging tool 206 can be transmitted to computing device 204 for storage, further processing (e.g., to generate a 3D reconstruction of the lumen being imaged), further transmission, etc. In various embodiments, OCT system 202 may simply transmit optical data to computing device 204 where the optical data would be digitized and stored, or OCT system 202 may digitize the data and transmit digitized data and/or reconstructed images to computing device 204.

In some embodiments, imaging tool 206 can include an optical waveguide (e.g., optical waveguide 106) and an optical imaging probe (e.g., optical imaging probe 104). In some embodiments, the optical imaging probe can be configured as a micro-OCT (µOCT) imaging probe. For example, the optical imaging probe can be configured to generate a beam with an extended depth of focus. In a more particular example, the optical imaging probe can be implemented using a mirror tunnel that can be used to generate an extended depth of focus beam (e.g., as described below in connection with FIGS. 4A to 4C). As another more particular example, the optical imaging probe can be implemented using apodizing optics that generate an extended depth of focus beam (e.g., as described below in connection with FIG. 4D). As yet another more particular example, an extended depth of focus can be produced using an axicon lens, a diffractive optical element, and/or a self-imaging wavelength division optics. In some embodiments, a reference reflector of OCT system 202 can be co-located with the optics at the distal end of imaging tool 206 (e.g., as described below in connection with optics 460 of FIG. 4D). In general, imaging tool 206 can be incorporated into a catheter-type device which can be used to guide imaging tool 206 into the round window and/or through the cochlea.

In some embodiments, as shown in FIG. 2, imaging tool 206 can be inserted into a subject's cochlea 208 via the round window 210, and the optical imaging probe can be advanced (as indicated by arrows in FIG. 2) through the scala tympani until a desired position is reached and/or until a safe distance between the optical imaging probe and the scala tympani can no longer be maintained (e.g., as described below in connection with FIG. 6).

Figure 3:
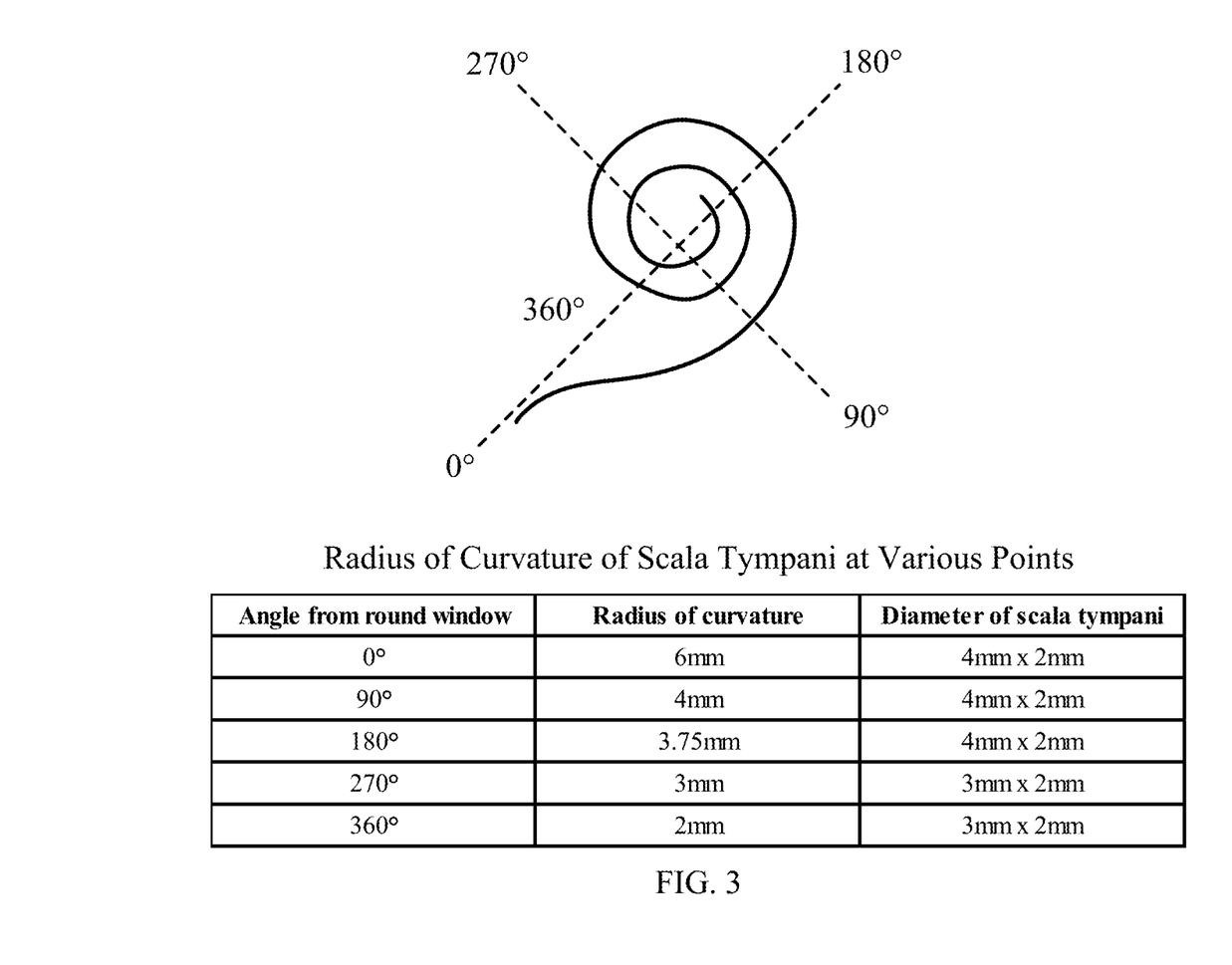
FIG. 3 shows the radius of curvature at various points in the cochlea.

FIG. 3 provides an example showing the radius of curvature at various points in the cochlea. As shown in FIG. 3, the cross-sectional area and radius of curvature of the scala tympani generally decrease as the distance from the round window increases. Note that at least some of the radii of curvature in the cochlea may be tighter than other luminal samples for which OCT is generally used (e.g., the gastrointestinal tract, the vascular system). Accordingly, in some embodiments, bends in the optical waveguide can cause loss of signal that does not occur in other luminal organs. Thus, in some embodiments, one or more techniques can be used to decrease bending losses in the optical waveguide. For example, bending losses can be reduced by incorporating a refractive index trench around the core of an optical fiber used to implement the optical waveguide. By increasing the difference between the refractive index of the optical fiber and the surrounding material, the critical angle can be reduced, thereby causing more light to be contained within the fiber core. As another example, bending losses can be reduced by surrounding the body of the optical waveguide (e.g., around the cladding) with a sheath infused with microscopic reflectors. In such an example, the microscopic reflectors can be implemented using microparticles and/or nanoparticles, a metallic coating, and/or a dielectric coating.

Figure 4A:
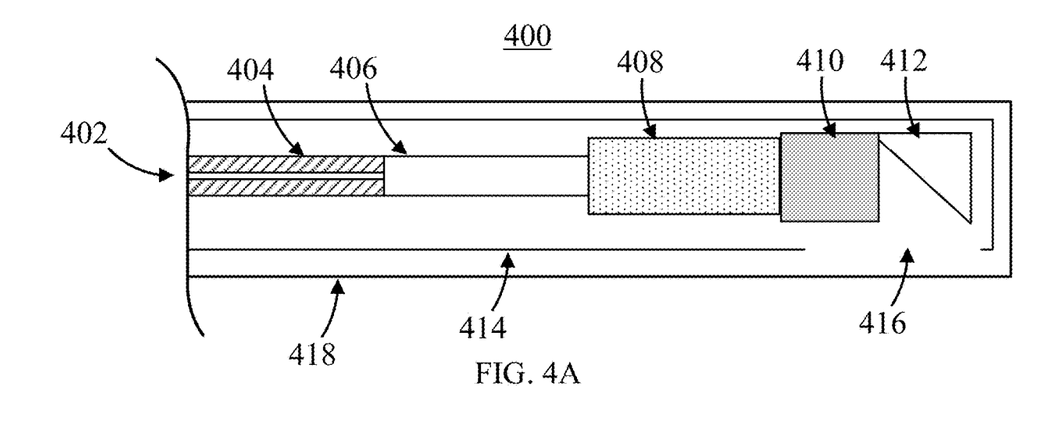
FIG. 4A shows an example of optics including a mirror tunnel and a gradient-index lens that can be used in a probe that generates a beam with an extended depth of focus for micro-optical coherence tomography imaging of the cochlea in accordance with some embodiments of the disclosed subject matter.

FIGS. 4A-4D show embodiments of optics that can be used in a probe according to embodiments of the disclosed subject matter. FIG. 4A shows an example 400 of optics including a mirror tunnel and a lens (e.g. a gradient-index (GRIN) lens) that can be used in a probe that generates a beam with an extended depth of focus for micro-optical coherence tomography imaging of the cochlea in accordance with some embodiments of the disclosed subject matter. As shown in FIG. 4A, optics 400 can include a single mode optical fiber 402 that can be used to implement optical waveguide 106. In some embodiments, optical fiber 402 can be fabricated with a Young's modulus of elasticity that is comparable to that of standard commercial cochlear implant electrode arrays. Optical fibers in general are significantly stiffer than cochlear implant electrode arrays, and thus is more susceptible to damage (e.g., fracture) as the radius of curvature decreases. Therefore, in some embodiments, the modulus of elasticity can be decreased using any suitable technique or combination of techniques. For example, in some embodiments, the distal end of optical fiber 402 (e.g., distal end 114) can be tapered in diameter so as to decrease the rigidity of the distal end of optical fiber 402. In a more particular example, the end of a standard communication grade optical fiber having a 125 micron (µm) or smaller diameter can be tapered down to a diameter in the range of about 5 to 50 µm. In another more particular example, the end of a standard communication grade optical fiber can be tapered to a diameter in the range of about 10 to 40 microns, 15 to 35 microns, or 20 to 30 microns. In some embodiments, the tapered portion of the optical fiber can extend through optics 400 (e.g., through a portion of optics 400 that may pass through the round window), and optical fiber 402 can increase in diameter near the distal end.

As another example, a coating (e.g., surrounding the cladding) of the optical fiber can be etched to decrease the amount of strain caused by a given radius of curvature. In a more particular example, the coating of optical fiber 402 can be etched using helical laser scribing techniques. In some embodiments, the pitch of the helical pattern can be adjusted along the length of the distal tip of the probe to provide flexibility gradients along the tip of the probe. For example, the helical pattern can be spaced closer together at the distal tip, and the spacing can be wider further from the distal tip such that optical fiber 402 becomes less flexible father from the tip.

As yet another example, in some embodiments, optical fiber 402 can be fabricated from a preform of highly elastic (e.g., having a Young's modulus of elasticity on the order of about 10 GPa or less) material using thermal drawing techniques to create an optical fiber with a relatively narrow diameters. As more particular example, materials that can be used to fabricate such an optical fiber include polyetherimide (e.g., having Young's modulus of about 3 GPa), polyphenylsulfone (e.g., having Young's modulus of about 2.3 GPa), polycarbonate (e.g., having a Young's modulus of about 2.38 GPa), and cyclic olefin copolymer (e.g., having a Young's modulus of about 3 GPa). Note that silicon optical fibers generally have a Young's modulus in the range of 130 to 188 GPa, while silica optical fibers generally have a Young's modulus in the range of about 69 GPa. Many implantable cochlear electrode arrays have a Young's modulus in the range of 180 to 500 GPa. Accordingly, using an optical imaging probe having a Young's modulus lower than the Young's modulus of implantable electrode arrays can insure that the probe can navigate anywhere the electrode array may be implanted.

In some embodiments, optics 400 can include a driveshaft 404 that is coupled to optical fiber 402 to provide a rotational force to optical fiber 402 and/or one or more other optical components. For example, driveshaft 404 can be rotated by a motor in an optical rotary joint, and can in turn cause optical fiber 402 to rotate. In some embodiments, driveshaft 404 can be omitted from a portion of optical fiber 402 that is to be inserted into a narrow and/or curved lumen (e.g., the cochlea). Alternatively, in some embodiments, a portion of driveshaft 404 that is to be inserted into a narrow and/or curved lumen can be configured to be more flexible than a portion of driveshaft 404 that is coupled to a mechanism that rotates driveshaft 404. For example, driveshaft 404 can be tapered. As another example, a lubricant (e.g., hyaluronic acid or glycerol) can be introduced around driveshaft 404. In some embodiments, driveshaft 404 can be terminated before a portion of a probe that is configured to be inserted, and can be coupled to a housing (e.g., housing 414 described below) surrounding optics 400 to cause the housing to rotate at the same rate as an optical fiber outside of the portion to be inserted.

In some embodiments, optics 400 can include a waveguide 406 (e.g., a multimode fiber or other optical waveguide of suitable diameter) can be coupled to a distal end of optical fiber 402 to form a mirror tunnel that can cause light emitted from optical fiber 402 to be emitted from waveguide 406 in multiple propagation modes.

In some embodiments, optics 400 can include a spacer 408 that can allow a diameter of one or more propagation modes of light emitted by waveguide 406 to expand.

In some embodiments, optics 400 can include a GRIN lens 410 that can focus a beam emitted by spacer 408 with a focal length approximately equal to the distance from a distal end of GRIN lens 410 to a surface of a sample (e.g., sample 120).

In some embodiments, optics 400 can include a prism 412 that can direct light focused by GRIN lens 410 toward a sample (e.g., sample 120). Additionally, in some embodiments, a surface of prism 412 can be coated with a reflective coating that can increase the amount of light reflected toward the sample. For example, prism 412 can redirect light emitted by GRIN lens 410 to an angle that is roughly perpendicular to the optical axis of GRIN lens 410.

In some embodiments, optics 400 can include a housing 414 (sometimes referred to herein as sleeve 414) into which the optical components may be disposed. In other embodiments, optics 400 can include an opening 416 in sleeve 414 that can allow light to be transmitted from prism 412 toward the sample. For example, opening 416 can be formed by removing a portion of sleeve 414 and/or by manufacturing sleeve 414 with an opening.

In some embodiments, optics 400 can include a sheath 418 into which optic 400 and/or sleeve 414 can be inserted; optics 400 and/or sleeve 414 can be rotatably disposed within sheath 418 to facilitate rotational scanning. In such embodiments, at least a portion of sheath 418 located near the distal tip of optics 400 can be transparent to facilitate transmission of light from prism 412 to a sample. In some embodiments, sheath 418 can be sealed to inhibit transfer of fluid, debris, and/or other material between an interior of sheath 418 and a lumen into which sheath 418 is inserted.

In some embodiments, waveguide 406, spacer 408, GRIN lens 410, and prism 412 (or a portion of these components) can be relatively rigid in comparison to optical fiber 402 and/or drive shaft 404, and the length of the rigid portion of these components can affect the radius of curvature through which optics 400 can be effectively bent. For example, as described above in connection with FIG. 3, the cochlea, particularly at its distal end, has a small diameter with a tapering radius of curvature. Accordingly, the rigid portion of optics 400 can limit the depth which optics 400 can be inserted into the cochlea insofar as the rigid portion of optics 400 may be unable to fit within the more distal parts of the cochlea where the radius of curvature is small. In some embodiments, the rigid length of optics 400 can be based on the desired depth of penetration into the cochlea, and the desired depth of focus, among other factors. For example, as the rigid length is reduced the depth of focus becomes smaller, but the maximum depth of penetration increases. In a more particular example, if optics 400 are configured to penetrate only 90 degrees (i.e., $\pi/2$ radians) into the cochlea, the rigid length can be longer (e.g., on the order of about 3-4 mm), which can accommodate optics that generate a relatively large depth of focus (e.g., on the order of about 1.5 mm). As another particular example, if optics 400 are configured to penetrate to about 360 degrees into the cochlea (i.e., $2\pi$ radians), the rigid length can be shorter (e.g., on the order of about 0.75 to 1.5 mm), which can accommodate optics that generate a shorter depth of focus.

In some embodiments, optics 400 can be fabricated to reduce the length of the rigid portion using one or more techniques. For example, the length of the rigid portion of optics 400 can be reduced by reducing the diameter of GRIN lens 410, which can facilitate a reduction in length (or elimination) of spacer 408. As another example, the length of the rigid portion of optics 400 can be reduced by reducing the length of the waveguide 406. As yet another example, in some embodiments, GRIN lens 410 and prism 412 can be replaced with a polished surface ball lens (e.g., as described below in connection with FIG. 4C). In some cases, shortening the length of the rigid portion of optics 400 can also reduce the depth of focus, potentially reducing the axial resolution of an OCT system implemented using optics 400.

In some embodiments, optics 400 can be fabricated to reduce nonuniform rotational distortion (NURD) using one or more techniques. For example, in some embodiments, a biocompatible lubricant can be introduced between driveshaft 404 and the inner wall of a sheath enclosing driveshaft 404, which can facilitate smoother rotation of optical fiber 402. As another example, prism 412 can be decoupled from GRIN lens 410, and can be rotated by a motor (e.g., a micromotor) while other portions of optics 400 remain static. In such an example, driveshaft 402 can be replaced as rotation of optical fiber 402 may be unnecessary.

Figure 4B:
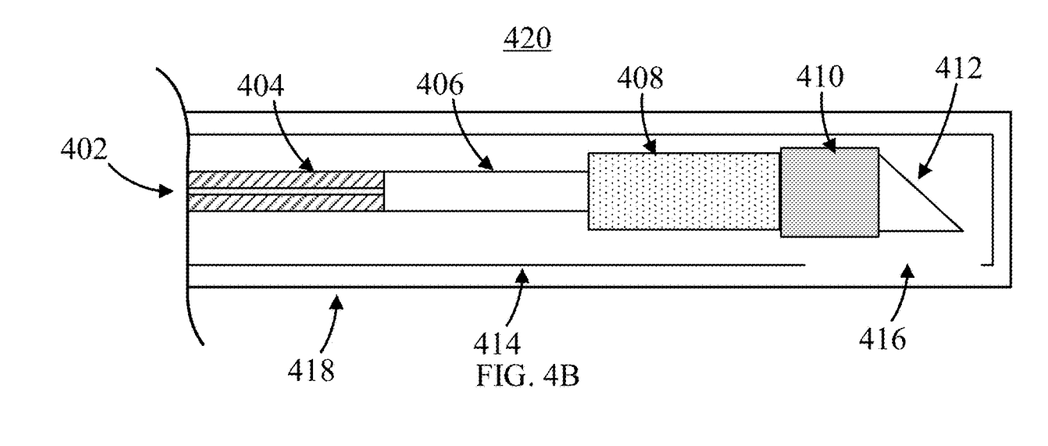
FIG. 4B shows another example of optics including a mirror tunnel and a gradient-index lens that can be used in a probe that generates a beam with an extended depth of focus for micro-optical coherence tomography imaging of the cochlea in accordance with some embodiments of the disclosed subject matter.

FIG. 4B shows another example 420 of optics including a mirror tunnel and a gradient-index lens that can be used in a probe that generates a beam with extended depth of focus for micro-optical coherence tomography imaging of the cochlea in accordance with some embodiments of the disclosed subject matter. As shown in FIG. 4B, optics 420 can be similar to optics 400, but with prism 412 rearranged such that light is emitted from GRIN lens 410 into prism 412, which reflects the light using an internal surface, and emits the light toward the sample. In some embodiments, one or more techniques described above in connection with FIG. 4A can be used in connection with optics 420 to reduce the length of the rigid portion of optics 420, to reduce NURD, etc.

Figure 4C:
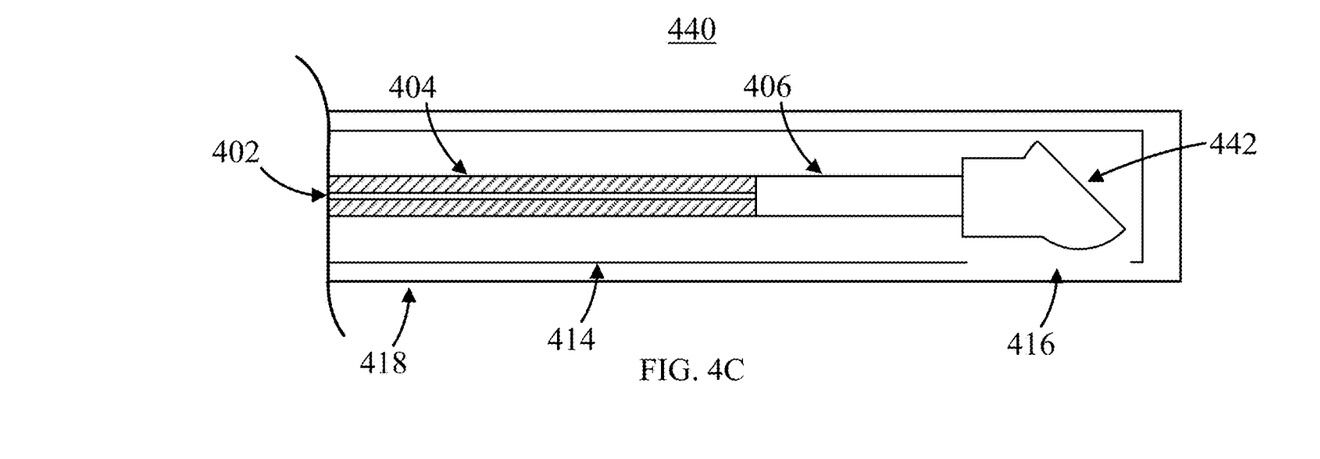
FIG. 4C shows an example of optics including a mirror tunnel and a ball lens that can be used in a probe that generates a beam with extended depth of focus for micro-optical coherence tomography imaging of the cochlea in accordance with some embodiments of the disclosed subject matter.

FIG. 4C shows an example 440 of optics including a mirror tunnel and a ball lens that can be used in a probe that generates a beam with extended depth of focus for micro-optical coherence tomography imaging of the cochlea in accordance with some embodiments of the disclosed subject matter. As shown in FIG. 4C, optics 440 can be similar to optics 400, but with spacer 408 and GRIN lens 410 replaced with ball lens 442, which can be used to reflect light toward the sample and to focus the light emitted by waveguide 406. In some embodiments, one or more techniques described above in connection with FIG. 4A can be used in connection with optics 440 to reduce the length of the rigid portion of optics 440, to reduce NURD, etc.

In some embodiments, optics 400, 420, and/or 440 can be implemented using one or more techniques for increasing depth of focus described in W.I.P.O. Application Publication No. WO 2017/049085, which is hereby incorporated by reference herein in its entirety.

Figure 4D:
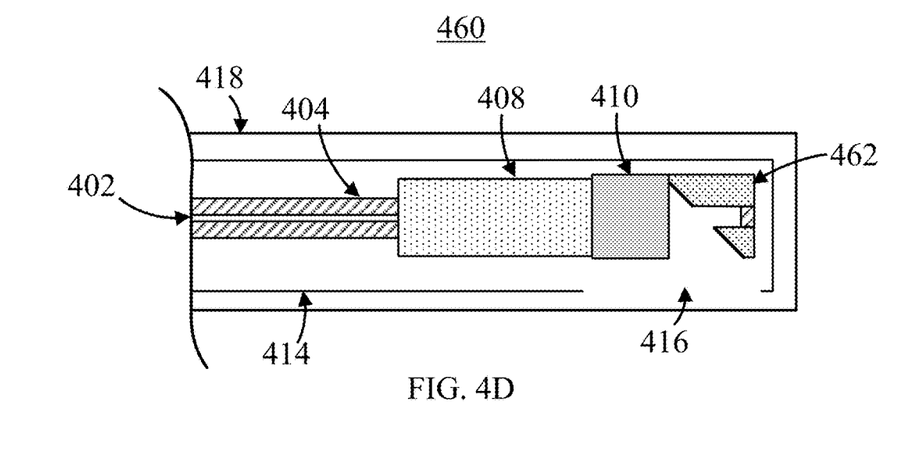
FIG. 4D shows an example of optics including a gradient-index lens and an apodizing mirror that can be used in a probe that generates a beam with extended depth of focus for micro-optical coherence tomography imaging of the cochlea in accordance with some embodiments of the disclosed subject matter.

FIG. 4D shows an example 460 of optics including a gradient-index lens and an apodizing mirror that can be used in a probe that generates a beam with extended depth of focus for micro-optical coherence tomography imaging of the cochlea in accordance with some embodiments of the disclosed subject matter. As shown in FIG. 4D, optics 460 can be similar to optics 400, but with waveguide 406 omitted and prism 412 replaced with an optical element 462 that has an angled reflective surface having a cylindrical bore, which can be used to reflect light toward the sample with an annular beam profile. In some embodiments, one or more techniques described above in connection with FIG. 4A can be used in connection with optics 460 to reduce the length of the rigid portion of optics 460, to reduce NURD, etc. In some embodiments, a reflective element can be incorporated into the cylindrical bore of optical element 462 to form a reference reflector for an OCT system to which optics 460 is coupled. In some embodiments, optics 460 can be implemented using one or more techniques for increasing depth of focus described in U.S. application Ser. No. 15/894,574, filed Feb. 12, 2018, which is hereby incorporated by reference herein in its entirety.

In some embodiments, a micromotor or nanomotor can be incorporated into optics described above in connection with FIGS. 4A to 4D, and can configured to rotate an optical element that reflects light toward the sample. Such a motor can be used to rotate the optical element to direct the light around a circumference of sheath 418. In such embodiments, the optical element that reflects light toward the sample (e.g., prism 412, ball lens 442, optical element 462) can be physically decoupled from a non-rotating portion of the optics (e.g., a non-rotating waveguide 406, a non-rotating GRIN lens 408, etc.).

Figure 5:
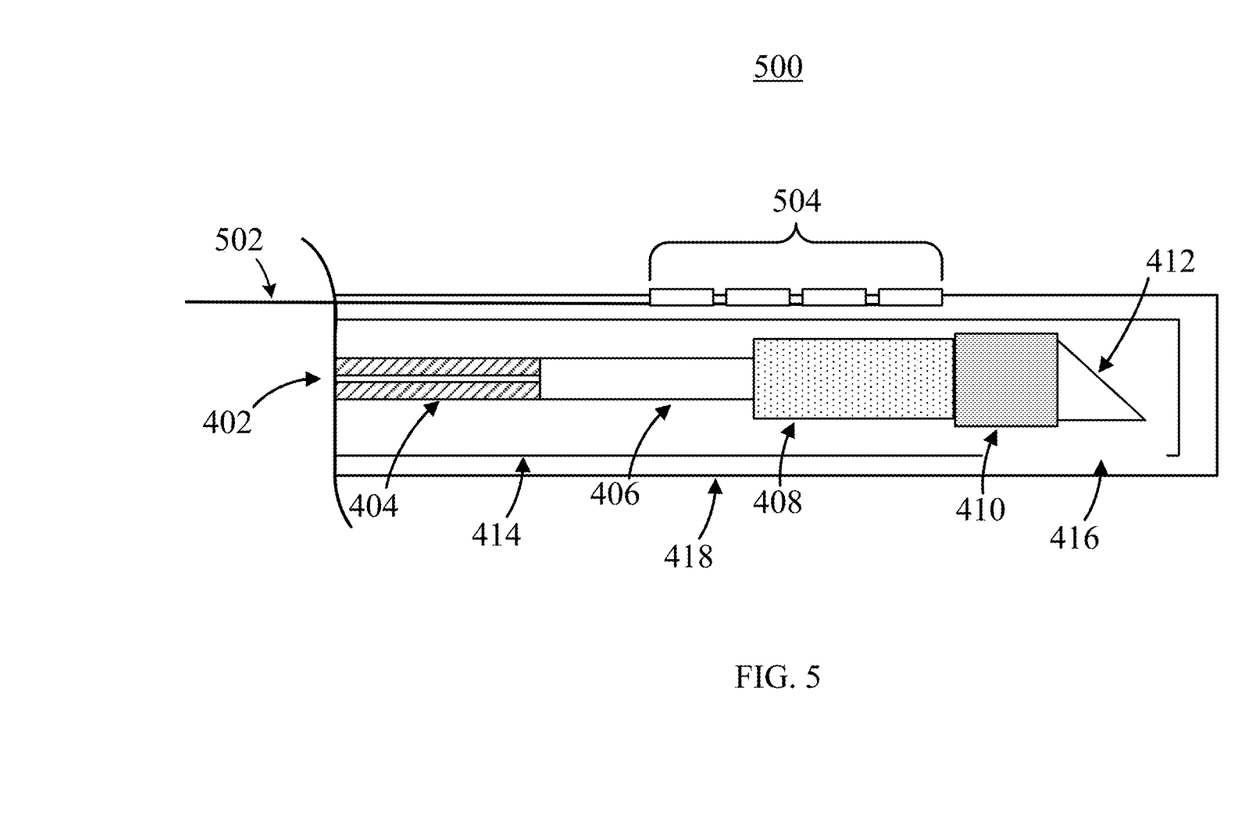
FIG. 5 shows an example of stimulators integrated into a probe for micro-optical coherence tomography imaging of the cochlea in accordance with some embodiments of the disclosed subject matter.

FIG. 5 shows an example 500 of stimulators and/or sensors integrated into a probe for micro-optical coherence tomography imaging of the cochlea in accordance with some embodiments of the disclosed subject matter. As shown in FIG. 5, optics 500 can include optics that are configured to perform μOCT (e.g., as described above in connection with FIGS. 4A to 4D), and can further include one or more conductors 502 (e.g., one or more wires) and one or more stimulators 504 that can be used to evaluate a subject's nerve function during scanning of the scala tympani. For example, in some embodiments, conductor(s) 502 can be integrated into a wall of sleeve 414. As another example, in some embodiments, conductor(s) 502 can pass through a secondary lumen of sleeve 414. In some embodiments, in addition to or in lieu of conductor 502 and stimulators 504, an additional lumen (e.g., the secondary lumen, or a third lumen) can be incorporated into sheath 418 that can be used to deliver fluid to, and/or collect fluid from, one or more lumina of the cochlea (e.g., to deliver therapy, to biopsy fluid in a lumen, etc.). In some embodiments, optics 500 can include one or more sensors (e.g., in addition to, or in lieu of, stimulators 504) that can be used to measure, for example, endocochlear potential.

In some embodiments, images captured using optics 500 during stimulation can be flagged (or otherwise designated) as corresponding to a particular stimulation (e.g., with identifying information of the stimulation, with a timestamp corresponding to the stimulation, etc.). In such examples, the location within the cochlea of the stimulation can be highlighted (or otherwise indicated) on a 2D and/or 3D reconstruction generated from images captured during the stimulation and/or images of the location at which stimulation was provided. In some embodiments, multiple wires can be used to connect different stimulators to a controller. Additionally or alternatively, in some embodiments, a single wire or set of wires can be used to connect multiple stimulators to the controller, and a signal emitted by the controller can be addressed to a particular stimulator(s).

Figure 6:
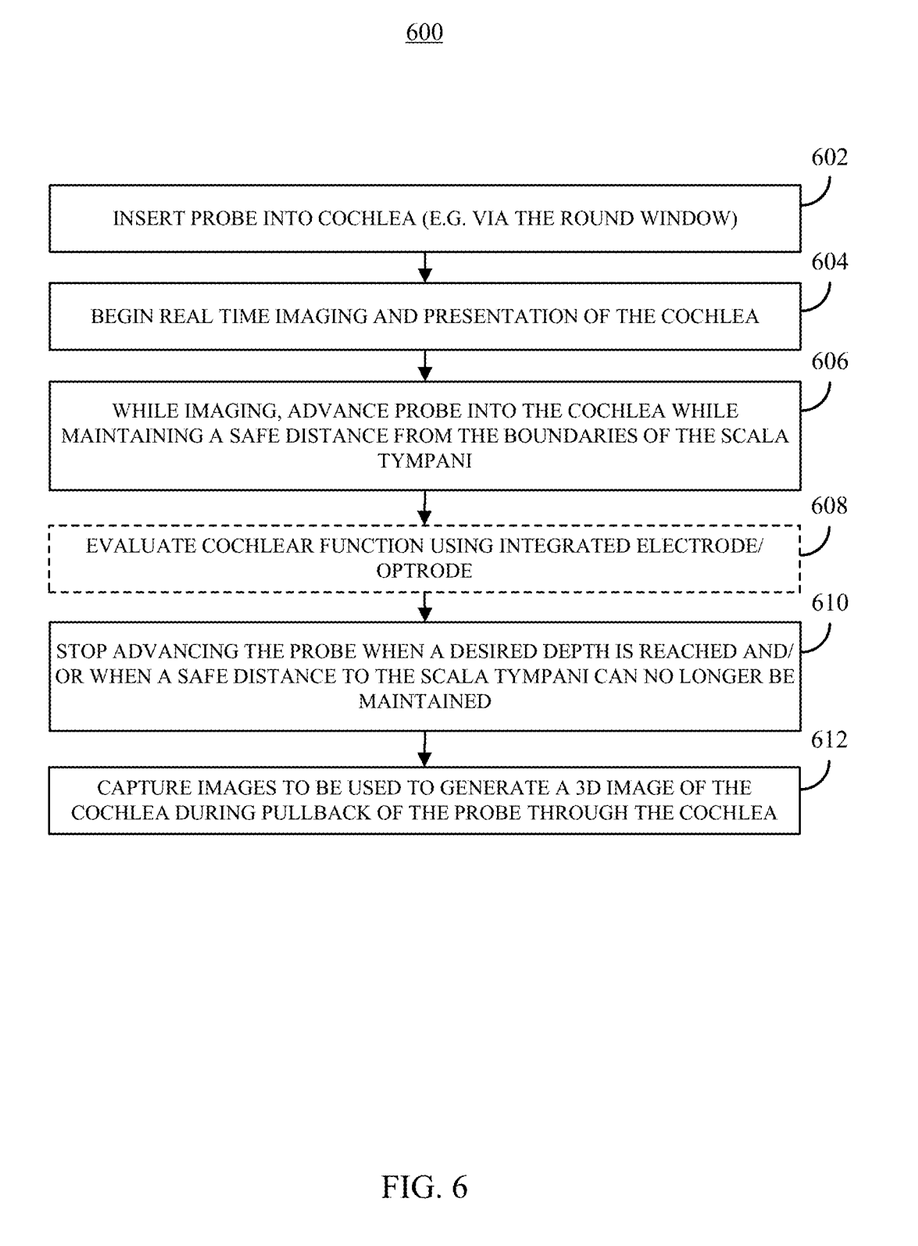
FIG. 6 shows an example of a process for micro-optical coherence tomography imaging of the cochlea in accordance with some embodiments of the disclosed subject matter.

FIG. 6 shows an example 600 of a process for micro-optical coherence tomography imaging of the cochlea in accordance with some embodiments of the disclosed subject matter. As shown in FIG. 6, process 600 can include inserting an optical probe into the cochlea of a subject. For example, the optical probe can be inserted via the round window into the scala tympani of the inner ear. In some embodiments, the optical probe inserted at 602 can be an OCT probe implemented using any suitable technique or combination of techniques. For example, in some embodiments, the probe can be a μOCT probe described above in connection with one or more of FIGS. 1 to 5.

At 604, process 600 can include causing an OCT system (e.g., OCT system 202) to begin generating real-time images of the cochlea of the subject as the optical probe is inserted. For example, in some embodiments, process 600 can generate 2D images of the cochlea based on A-scans of the cochlea, and can display the 2D images (e.g., as shown in, and described below in connection with, FIG. 8A) and/or 3D reconstructions (e.g., as shown in, and described below in connection with, FIG. 8B).

At 606, process 600 can include advancing the optical probe into the cochlea while maintaining a safe distance from the subject's anatomy (e.g., the boundaries of the scala tympani). For example, in some embodiments, while a user (e.g., a surgeon) is advancing the optical probe through the scala tympani, the surgeon can view the real time images to maintain a safe distance between the probe and portions of the subject's anatomy, such as the basilar membrane, or the wall of the cochlea (depending on the current depth of insertion).

At 608, in some embodiments, process 600 can include evaluating cochlear function using one or more integrated electrodes and/or optrodes. For example, if an optical probe that includes integrated stimulators is used (e.g., as described above in connection with FIG. 5), during insertion (and/or during pullback) stimulation can be provided to one or more portions of the auditory nerve, and the points at which stimulation was provided can be recorded such that a particular stimulation can be associated with a particular result.

At 610, process 600 can include inhibiting advancement of the optical probe when a desired depth of insertion has been reached and/or when a safe distance to the subject's anatomy can no longer be maintained. For example, in some embodiments, a user can determine that the distance between the optical probe and the boundary of the scala tympani is small enough that further advancement of the optical probe is likely to cause a collision with a portion of the subject's anatomy.

At another example, a user can determine, based on the amount of the optical fiber that has been inserted that a desired depth of insertion has been reached. As yet another example, based on one or more portions of the subject's anatomy, a user can determine that a desired depth of insertion has been reached.

At 612, process 600 can include capturing data during a pullback operation that can be used to generate a 3D image of the subject's anatomy. For example, in some embodiments, a user can initiate a pullback operation (which can be performed manually and/or with the assistance of one or more components that can control a speed of the pullback), and input can be provided that can be used to determine which data was captured before the pullback was initiated and/or to determine which data was captured during the pullback operation.

In some embodiments, the optical probe can be positioned prior to and/or during pullback such that the field of view of the optical probe during the pullback includes one or more anatomical features of the subject's cochlea. For example, the optical probe can be positioned during pullback such that anatomical features described below in connection with FIG. 7 are included in the field of view (if present in the subject's cochlea).

Figure 7:
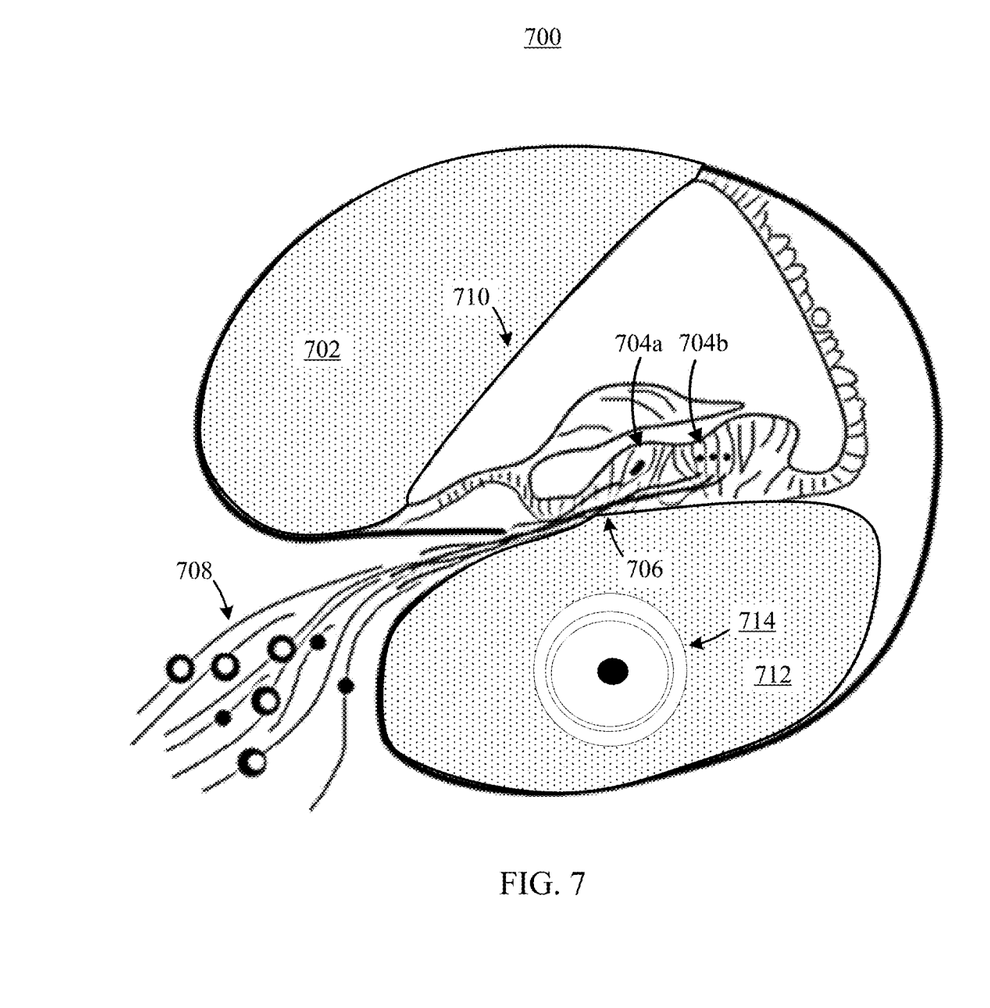
FIG. 7 shows an example of a cross section of the cochlea including various anatomical features that can be imaged using mechanisms described herein for micro-optical coherence tomography imaging of the cochlea.

FIG. 7 shows an example 700 of a cross section of the cochlea including various anatomical features that can be imaged using mechanisms described herein for micro-optical coherence tomography imaging of the cochlea. As shown in FIG. 7, cochlea 700 can include the scala vestibuli 702 and the scala tympani 712 which form the respective inner and outer portions of the spiral-shaped cochlea, such that the scala vestibuli 702 and the scala tympani, which surround other portions of the inner ear, are shown. For example, cochlea 700 can include inner 704a and outer 704b hair cells, auditory nerve fibers 706, spiral ganglion neuron cell bodies 708, and Reissner's membrane 710. Additionally, shown in FIG. 7 is a cross section 714 of a portion of an optical probe that can be used to capture data that can be used to generate OCT images of cochlea 700.

Figure 8A:
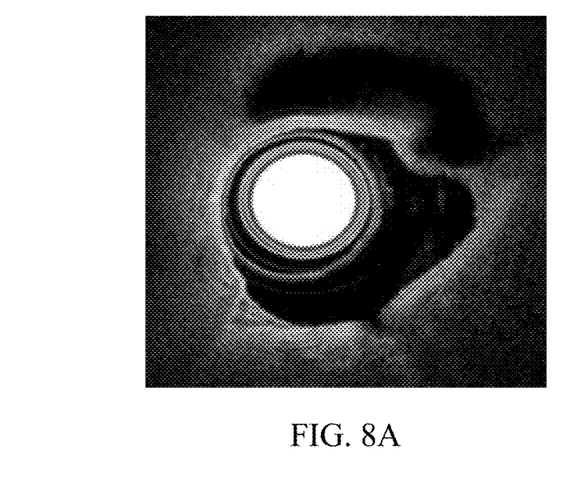
FIG. 8A shows an example of a two dimensional cross section of a cochlea generated using a system for micro-optical coherence tomography imaging implemented in accordance with some embodiments of the disclosed subject matter.

FIG. 8A shows an example of a two-dimensional cross section of a cochlea generated using a system for micro-optical coherence tomography imaging implemented in accordance with some embodiments of the disclosed subject matter.

Figure 8B:
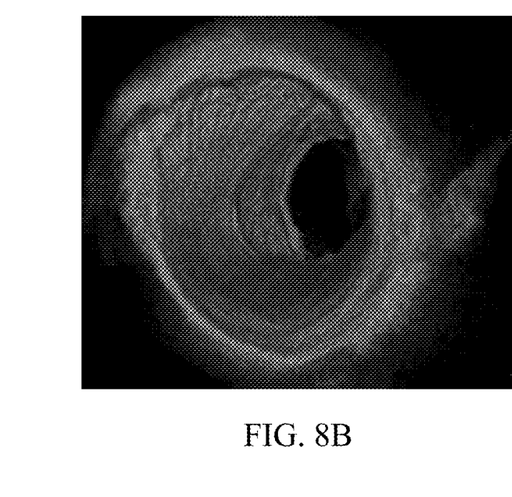
FIG. 8B shows an example of a three-dimensional reconstruction of the scala tympani of a cochlea generated using images from a system for micro-optical coherence tomography imaging implemented in accordance with some embodiments of the disclosed subject matter.

FIG. 8B shows an example of a three-dimensional reconstruction of the scala tympani of a cochlea generated using images from a system for micro-optical coherence tomography imaging implemented in accordance with some embodiments of the disclosed subject matter.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the process of FIG. 6 can be executed or performed in any order or sequence not limited to the order and sequence shown and described in the figures. Also, some of the above steps of the processes of FIG. 6 can be executed or performed substantially simultaneously where appropriate or in parallel to reduce latency and processing times.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. An optical coherence tomography (OCT) imaging tool, comprising:

a first optical waveguide having a proximal end and a distal end,
the first optical waveguide comprising a single mode optical fiber and configured to transmit light between the proximal end and the distal end of the first optical waveguide,
the single mode optical fiber comprising a proximal end and a distal end is tapered from a diameter of 125 μm at the proximal end to a diameter between 5 μm and 50 μm at the distal end, and
at least a portion of the first optical waveguide in which the light is transmitted disposed at the distal end of the first optical waveguide having an increased flexibility with respect to the proximal end of the first optical waveguide;
a sheath surrounding at least the portion of the first optical waveguide; and
an optical probe coupled to the first optical waveguide, the optical probe comprising:
a housing rotatably disposed within the sheath;
an optical element disposed within the housing, the optical element comprising a reflective surface, the optical element being coaxially aligned with a central axis of the distal end of the first optical waveguide,
the optical element being configured to rotate about the central axis and redirect light emitted by the first optical waveguide toward a circumference of the optical probe from the central axis;
a second optical waveguide having a proximal end and a distal end, the proximal end of the second optical waveguide being directly coupled to the distal end of the first optical waveguide,
the second optical waveguide being configured to act as a mirror tunnel that causes light that is emitted from the distal end of the first optical waveguide and received at the proximal end of the second optical waveguide with a single propagation mode to be emitted from the distal end of the second optical waveguide with multiple propagation modes; and
a spacer directly coupled to the distal end of the second optical waveguide,
the OCT imaging tool being configured to resolve micron-scale anatomical features, and
the optical probe comprising a rigid portion comprising the second optical waveguide and the spacer, and
the rigid portion of the optical probe having a length of between 0.75 mm to 1.5 mm and being configured to insert into a structure with a radius of curvature of between 2-6 mm.

2. The OCT imaging tool of claim 1, wherein the first optical waveguide comprises an optical fiber core and a refractive index trench coaxially surrounding the optical fiber core.

3. The OCT imaging tool of claim 1, wherein the portion of the first optical waveguide having an increased flexibility comprises an optical fiber surrounded by a cladding which is etched to remove material around the circumference of the first optical waveguide, thereby decreasing the Young's modulus of elasticity of the portion of the first optical waveguide.

4. The OCT imaging tool of claim 1, wherein the second optical waveguide comprises a multimode optical fiber.

5. The OCT imaging tool of claim 1, wherein the optical element is a prism, and wherein the optical probe further comprises a gradient index (GRIN) lens disposed between the spacer and the optical element.

6. The OCT imaging tool of claim 1, wherein the optical element is a polished ball lens.

7. The OCT imaging tool of claim 1, further comprising:
a stimulator configured to provide stimulation to a portion of an auditory nerve of a subject; and
a conductor coupled to the stimulator, wherein the conductor is configured to transmit a signal to the stimulator.

8. The OCT imaging tool of claim 1, wherein the first optical waveguide is configured to rotate within the sheath.

9. The OCT imaging tool of claim 1, further comprising a driveshaft coupled to the optical element and surrounding the first optical waveguide, the second optical waveguide, or both, such that rotation of the driveshaft causes the first optical waveguide to rotate within the sheath.

10. The OCT imaging tool of claim 7, wherein the stimulator comprises an electrode disposed at an exterior surface of the sheath.

11. The OCT imaging tool of claim 7, wherein the stimulator comprises an optrode disposed at an exterior surface of the sheath.

12. The OCT imaging tool of claim 7, wherein the conductor is integrated into the sheath.

13. The OCT imaging tool of claim 7, wherein the first optical waveguide is disposed within a first lumen of the sheath, and the conductor is disposed within a second lumen of the sheath.

14. A method for micro-optical coherence tomography imaging of a human cochlea in vivo, comprising:
emitting, by a source coupled to a first optical waveguide, light into a proximal end of the first optical waveguide toward a distal end of the first optical waveguide that is coupled to an optical imaging probe inserted into the cochlea through the round window of the cochlea,
the first optical waveguide comprising:
at least a portion of the first optical waveguide comprising a single mode optical fiber and configured such that the light is transmitted disposed at the distal end of the first optical waveguide having an increased flexibility with respect to the proximal end of the first optical waveguide,
the single mode optical fiber comprising a proximal end and a distal end and is tapered from a diameter of 125 μm at the proximal end to a diameter between 5 μm and 50 μm at the distal end, and
a sheath surrounding at least the portion of the first optical waveguide, and the optical imaging probe comprising:
a housing rotatably disposed within the sheath,
an optical element disposed within the housing, the optical element comprising a reflective surface, the optical element being coaxially aligned with a central axis of a distal end of the first optical waveguide,
the optical element being configured to rotate about the central axis and redirect light emitted by the first optical waveguide toward a circumference of the optical probe from the central axis,
a second optical waveguide having a proximal end and a distal end, the proximal end of the second optical waveguide being directly coupled to the distal end of the first optical waveguide,
the second optical waveguide being configured to act as a mirror tunnel that causes light that is emitted from the distal end of the first optical waveguide and received at the proximal end of the second optical waveguide with a single propagation mode to be emitted from the distal end of the second optical waveguide with multiple propagation modes, and a spacer directly coupled to the distal end of the second optical waveguide, the optical probe comprising a rigid portion comprising the second optical waveguide and the spacer, and the rigid portion of the optical probe having a length of between 0.75 mm to 1.5 mm and being configured to insert into a portion of the human cochlea with a radius of curvature of between 2-6 mm causing, while rotating the housing within the sheath, the optical imaging probe to emit light received from the distal end of the first optical waveguide toward an interior of the cochlea;

causing, while rotating the housing within the sheath, the optical imaging probe to receive reflected light from the cochlea and transmit the reflected light toward a proximal end of the first optical waveguide;

receiving, using an optical coherence tomography system, the reflected light from the optical imaging probe;

generating, using the optical coherence tomography system, a two dimensional image of a portion of the cochlea surrounding the optical probe based on the reflected light received from the optical imaging probe; and causing the two dimensional image of the portion of the cochlea surrounding the optical probe to be presented, the two dimensional image being indicative of a radial distance between an outer surface of the optical probe and a wall of the cochlea, and the two-dimensional image comprising information identifying micron-scale anatomical features.

15. The method of claim 14, further comprising causing a series of two dimensional images to be generated based on reflected light received from the optical probe during a pullback operation in which the optical probe is extracted from the cochlea.

16. The method of claim 15, further comprising generating a three-dimensional reconstruction of the scala tympani of the cochlea based on the series of two dimensional images.

17. The method of claim 14, wherein the two dimensional image is a first two dimensional image, the method further comprising:

causing stimulation to be provided to a portion of an auditory nerve of a subject via a stimulator positioned proximate to the optical probe concurrently with causing the optical imaging probe to emit light received from the distal end of the first optical waveguide toward the interior of the cochlea;

recording a point in time at which the stimulation was provided; and associating a second two dimensional image of the cochlea generated using light received concurrent with the point in time at which the stimulation is provided, wherein the second two dimensional image is different from the first two dimensional image.

18. An optical coherence tomography (OCT) imaging tool, comprising:

a first optical waveguide having a proximal end and a distal end, the first optical waveguide comprising a single mode fiber and configured to transmit light between the proximal end and the distal end of the first optical waveguide, the single mode fiber comprising a proximal end and a distal end and is tapered from a diameter of 125 µm at the proximal end to a diameter between 5 µm and 50 µm at the distal end, at least a portion of the first optical waveguide in which the light is transmitted disposed at the distal end of the first optical waveguide having an increased flexibility with respect to the proximal end of the first optical waveguide, and the first optical waveguide comprising an optical fiber, a proximal end of the optical fiber having a first diameter, and the optical fiber tapering to a distal section having a second diameter that is smaller than the first diameter such that the portion of the first optical waveguide comprises the distal section of the optical fiber having the second diameter;

a sheath surrounding at least the portion of the first optical waveguide; and an optical probe coupled to the first optical waveguide, the optical probe comprising:

a housing rotatably disposed within the sheath;

an optical element disposed within the housing, the optical element comprising a reflective surface, the optical element being coaxially aligned with a central axis of the distal end of the first optical waveguide, the optical element further comprising a driveshaft coupled to the optical element and surrounding the first optical waveguide such that rotation of the driveshaft causes the first optical waveguide to rotate within the sheath, a lubricant being included around the driveshaft, and the optical element being configured to rotate about the central axis and redirect light emitted by the first optical waveguide toward a circumference of the optical probe from the central axis;

a second optical waveguide having a proximal end and a distal end, the proximal end of the second optical waveguide being directly coupled to the distal end of the first optical waveguide, the second optical waveguide being configured to act as a mirror tunnel that causes light that is emitted from the distal end of the first optical waveguide and received at the proximal end of the second optical waveguide with a single propagation mode to be emitted from the distal end of the second optical waveguide with multiple propagation modes; and a spacer directly coupled to the distal end of the second optical waveguide, the OCT imaging tool being configured to resolve micron-scale anatomical features, the optical probe comprising a rigid portion comprising the second optical waveguide and the spacer, and the rigid portion of the optical probe having a length of between 0.75 mm to 1.5 mm and being configured to insert into a structure with a radius of curvature of between 2-6 mm.

* * * * *